United States Patent
Toyoda et al.

(10) Patent No.: US 6,932,920 B2
(45) Date of Patent: Aug. 23, 2005

(54) COMPLEX MATERIAL, ARTIFICIAL LIGHT-EMITTING SKIN AND ARTIFICIAL LIGHT-EMITTING BODY

(75) Inventors: Junichi Toyoda, Tokyo (JP); Masayuki Suzuki, Kanagawa (JP); Naomi Nagasawa, Kanagawa (JP)

(73) Assignee: Son Corporation, Tokyo (JP)

( * ) Notice: Subject to any disclaimer, the term of this patent is extended or adjusted under 35 U.S.C. 154(b) by 0 days.

(21) Appl. No.: 10/683,045

(22) Filed: Oct. 14, 2003

(65) Prior Publication Data

US 2004/0135121 A1 Jul. 15, 2004

(30) Foreign Application Priority Data

Oct. 17, 2002 (JP) .......................................... 2002-302451

(51) Int. Cl.⁷ .......................... C09K 11/08; C09K 11/64
(52) U.S. Cl. .................................. 252/301.36; 428/690
(58) Field of Search ....................... 252/301.36; 428/690

(56) References Cited

U.S. PATENT DOCUMENTS 6,628,375 B2 * 9/2003 Xu et al. ....................... 356/32
2003/0205092 A1 * 11/2003 McElhanon et al. .......... 73/800
2004/0120684 A1 * 6/2004 Ishibashi et al. ............. 385/141

FOREIGN PATENT DOCUMENTS

WO  WO 01/48115  * 7/2001

OTHER PUBLICATIONS

60/169433.*

* cited by examiner

Primary Examiner—C. Melissa Koslow
(74) Attorney, Agent, or Firm—Oblon, Spivak, McClelland, Maier & Neustadt, P.C.

(57) ABSTRACT

A complex material, which emits light with a light hand or finger touch of a person and only when subjected to a stress, comprises stress emission particles and an elastic material. The stress emission particles such as $SrAl_2O_4$:Eu particles emit light when subjected to a stress. The elastic material is a soft material having a Young's modulus smaller than 10 MPa, such as silicone rubber, synthetic rubber, natural rubber, or the like. Weight percent of the particles in the complex material is from equal to or more than 10% to less than 100%, ore preferably from equal to or less more than 10% to equal to or less than 90%. The particles are preferably surface-treated by a silane coupling agent. The complex material is used as an artificial light-emitting skin or an artificial light-emitting body.

1 Claim, 11 Drawing Sheets

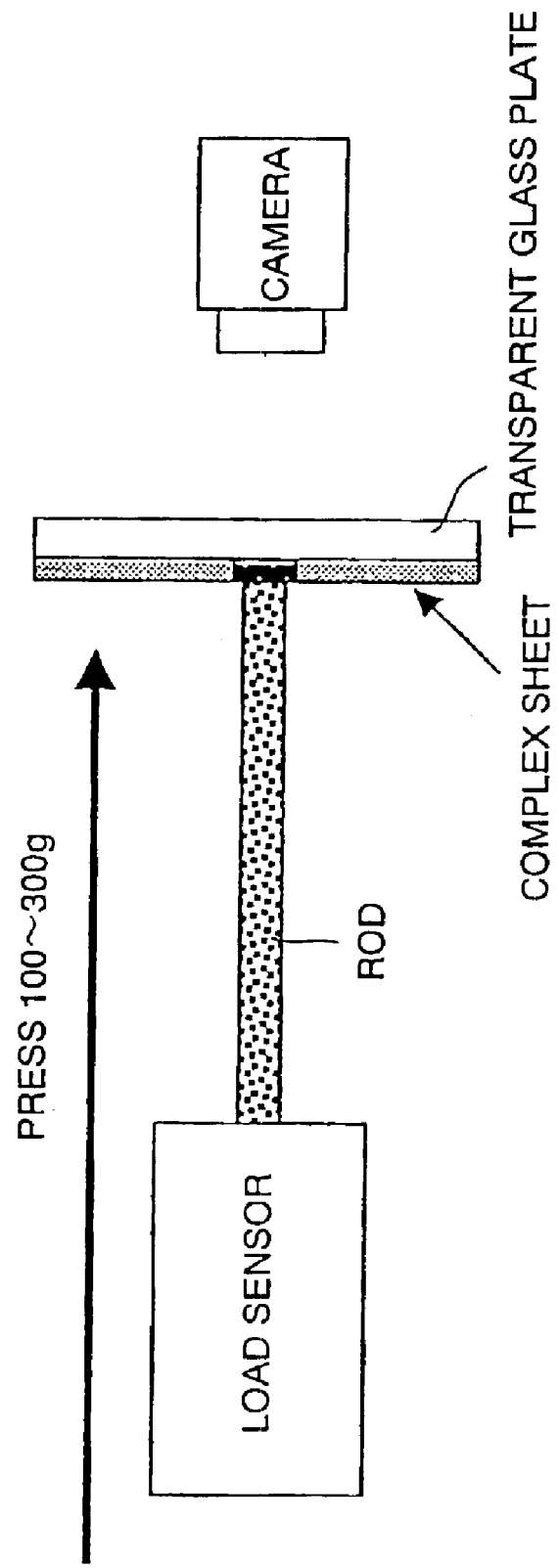

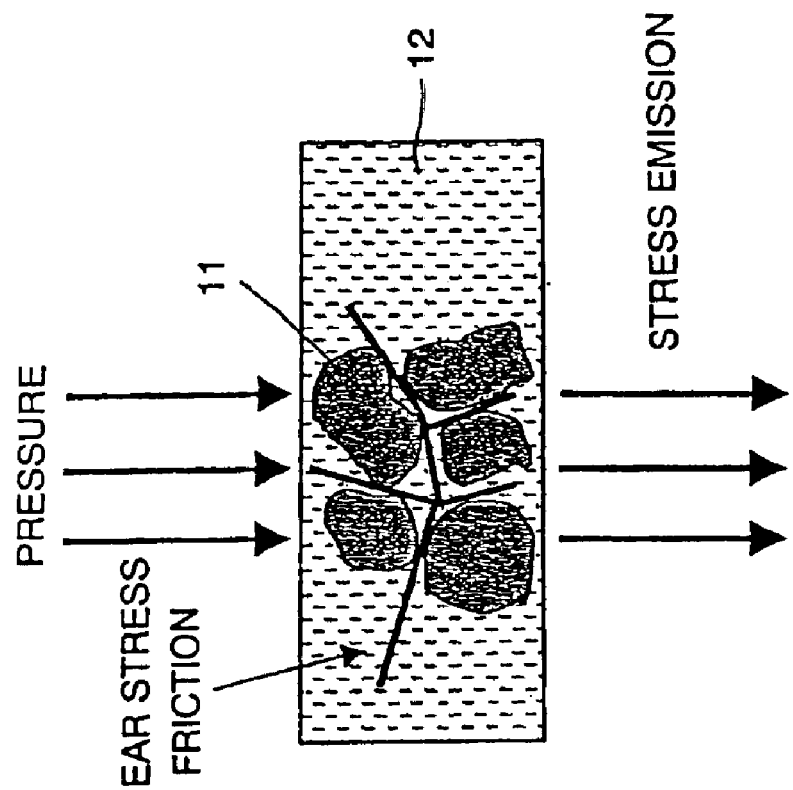
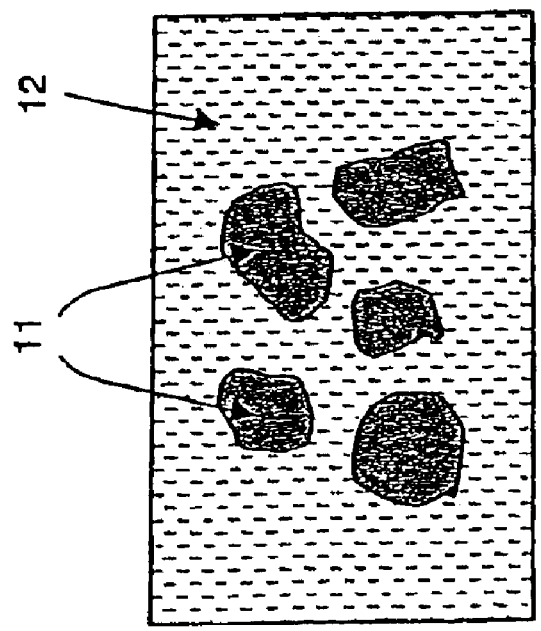

EMISSION OF LIGHT AT THE INSTANT OF A STRETCH

ASPECT IN DARK

ASPECT OF STRETCHER AND SAMPLE UNDER LIGHT

COMPLEX MATERIAL, ARTIFICIAL LIGHT-EMITTING SKIN AND ARTIFICIAL LIGHT-EMITTING BODY

BACKGROUND OF THE INVENTION

1. Field of the Invention

This invention relates to a complex material, artificial light-emitting skin and artificial light-emitting body that are suitable for use, for example, in the field of entertainment or amusement using emission of light effectively.

2. Description of the Related Art

For years, aluminate compound materials doped with rare earth elements have been remarked as fluorescent materials, and have been under vigorous researches. Among various aluminate compound materials, Eu-doped $SrAl_2O_4$ (named $SrAl_2O_4$:Eu herein below) has attracted the greatest attention as from a report on the phenomenon of stress emission as introduced herein below. Thus, prehistory of researches and developments of this $SrAl_2O_4$:Eu is first explained below while citing prior art documents.

History of Patents and Researches of $SrAl_2O_4$:Eu as Fluorescent Material $SrAl_2O_4$:Eu has the prehistory of having been studies as a fluorescent material from a long time ago. U.S. Pat. No. 3,294,699 on this material issued already in the 1960s, and the material is currently one of known materials.

History of Inventions and Researches of Phosphorescent Material/Long-afterglow Phosphor $SrAl_2O_4$:Eu+Dy (Brand Name "LumiNova") by Nemoto & Co., Ltd.

There are many reports and commentaries on this phosphor, some of which are listed below.

Non-patent Document 1:
URL: http://www/nemoto.co.jp/index_j.html accessed through the Internet on Aug. 30, 2002

Non-Patent Document 2:
URL: http://www/nemoto.co.jp/products/luminova/index.html accessed through the Internet on Aug. 30, 2002

Non-Patent Document 3:
URL: http://www/nemoto.co.jp/product/01_luminova/index.html accessed through the Internet on Aug. 30, 2002

Non-Patent Document 4:
URL: http://www/nemoto.co.jp/column/10_glow.html accessed through the Internet on Aug. 30, 2002

Patent Document 2:
Specification of Japanese Patent No. 2543825

Patent Document 3:
Specification of U.S. Pat. No. 5,424,006

Patent Document 4:
Specification of European Patent No. 622440

Non-patent Document 5:
T. Matsuzawa, N. Takeuchi, Y. Aoki and Y. Murakami, 248th Lecture Papers of Phosphor Research Society "Proc. Phosphor Res. Soc." (1993 Nov. 26) 7–13

Non-patent Document 6:
Yoshihiko Murakami, Nikkei Science, 5(1996) 20–29

Non-patent Document 7:
T. Matsuzawa, Y. Aoki, T. Takeuchi and Y. Murayama, J. Electrochem. Soc., 143(1996) 2670–2673

Non-patent Document 8:
Ceramics, 32(1997) 40–43

Non-patent Document 9:
Y. Murakami, Hakaru, 42(1997) 2–7

Discovery of Stress Emission in $SrAl_2O_4$:Eu Compound Materials by C- N. Xu, et al. of National Institute of Advanced Industrial Science and Technology (AIST), Institute for Structural and Engineering Materials (ISEM), Multifunctional Materials Technology Group (Former, MITI Institute for Industrial Technology, Kyushu Institute for Industry and Technology, Laboratory for Inorganic Complex Materials and Functional Ceramics) as well as History of Related Patents and Researches There are many commentaries and reports on the stress emission $SrAl_2O_4$:Eu compound materials and related substances, such as, for example, Non-patent Documents 10–17 and Patent Documents 5–19 that are listed below.

Non-patent Document 10: C- N. Xu, AIST Today, vol. 2, No. 8 (2002)

Non-patent Document 11: URL:
http//www.aist.go.jp/aist$_{13}$ j/aistinfo/aist_today/vol02_08/vol02_80_main.html accessed through the Internet on Aug. 30, 2002

Non-patent Document 12: URL:
http//www.aist.go.jp/aist_j/aistinfo/aist_today/vol02_08/vol02_08_p13.pdf accessed through the Internet on Aug. 30, 2002

Non-patent Document 13: C- N. Xu, T. Watanabe, M. Akiyama and X- G. Zheng, Appl. Phys. Lett., 74(1999) 1236–1238

Non-patent Document 14: C- N. Xu, T. Watanabe, M. Akiyama and X- G. Zheng, Appl. Phys. Lett., 74(1999) 2414–2416

Non-patent Document 15: C- N. Xu, X- G Zheng, M. Akiyama, K. Nonaka and T. Watanabe, Appl. Phys. Lett., 76(2000)179–181

Non-patent Document 16: C- N. Xu, Kagaku Kogyo (October 2000) pp. 790–794 & 808

Non-patent Document 17: C- N. Xu, Gekkan Display, September (2001) 98–103

Patent Document 5: Japanese Laid-open Publication JP-1999-116946-A

Patent Document 6: Specification of Japanese Patent No. 3265356

Patent Document 7: Specification of Japanese Patent No. 3136340

Patent Document 8: Specification of Japanese Patent No. 3136338

Patent Document 9: Specification of Japanese Patent No. 2992631

Patent Document 10: Japanese Patent Laid-open Publication JP-2000-313878-A

Patent Document 11: Japanese Patent Laid-open Publication JP-2001-49251-A

Patent Document 12: Japanese Patent Laid-open Publication JP-2001-123162-A

Patent Document 13: Japanese Patent Laid-open Publication JP-2001-215157-A

Patent Document 14: Specification of Japanese Patent No. 3273317

Patent Document 15: Japanese Patent Laid-open Publication JP-2002-194349-A

Patent Document 16: Japanese Patent Laid-open Publication JP-2002-194350-A

Patent Document 17: Japanese Patent Laid-open Publication JP-2002-201068-A

Patent Document 17: Specification of U.S. Pat. No. 6,117,574

Patent Document 18: Specification of U.S. Pat. No. 6,159,394

Patent Document 5 discloses materials that contain 0.01~20 weight percent of rare earths or transition metals and emit light with external mechanical energy received by a wurzite type piezoelectric material. Patent Document 6 discloses thin films of these materials. Patent Document 7 discloses materials that contain transition elements or rare earth elements having electron shells of $3d$, $4d$, $5d$ and $4f$ added to $MgAl_2O_4$, $CaAl_2O_4$, $Al_2O_3$ and $SrMgAl_{10}O_{17}$ as their matrices and emit light upon deformation with a mechanical external force, as well as a manufacturing method thereof. Patent Document 8 discloses materials that are made of substances containing transition elements or rare earth elements having electron shells of $3d$, $4d$, $5d$ and $4f$ and added to matrix crystals of metal oxides/complex oxides, and emit light by mechanical deformation. Patent Document 9 discloses materials containing transition elements or rare earths added to matrix materials of $Sr_3Al_2O_6$ and $Ga_3Al_2O_6$, as well as a manufacturing method thereof by baking under a controlled amount of the additive substance in 0.01~20 weight percent in a reducing atmosphere adjusted to 800–1700° C. Patent Document 10 discloses materials containing rare earths or transition metal elements as emission centers added to matrix materials of Y-Ba-Mg-Si oxides, which convert external mechanical energy to light. Patent Document 11 describes materials that contain regulated aluminate having a non-stoichiometrical composition and emit light under mechanical energy. Patent Document 12 describes $mMO \cdot nAl_2O_3$ materials as phosphorus memory excited by visible light. Patent Document 13 discloses a system for measuring the stress profile by using a stress emission material. Patent Document 14 discloses materials that contain oxides having a melilite type crystal structure (such as $CaYAl_2O_7$, $Ca_2Al_2SiO_7$ or the like) as their matrices and emit light under mechanical energy. Patent Document 15 discloses materials $MN_2O_4$, where M=Mg, Sr, Ba or Zn, N=Ga or Al, doped with rare earths or transition metals as their emission centers, together with a manufacturing method thereof. Patent Document 16 describes field emission materials composed of aluminate as their matrices and containing doped rare earths or transition elements. Patent Document 17 discloses electrostriction materials of (Sr, Ba, Mg, Ca, Zn, Cd)–(Al, Ga, Si) oxides having the maximum distortion of 1%. This is a considerably large value. Patent Document 18 discloses piezoelectric materials among triboluminescent materials. Patent Document 19 mainly describes $Sr_3Al_3O_6$ among stress emission materials, and this document corresponds to Patent Document 9.

Next explained are prior art technologies for complexing stress emission substances, mainly $SrAl_2O_3$, and resins.

Products incorporating complex materials commercially named "LumiNova" ($SrAl_2O_4$:Eu+Dy) into resins are on sale in form of "incorporated resin pellets" from Nemoto & Co., Ltd. They are introduced in the web sites, URL: http://www.nemoto.co.jp/products/luminova/index.html accessed through the Internet on Aug. 30, 2002 and herein taken as Non-patent Document 18, and URL: http://www.nemoto.co.jp/products/gss/index.html accessed through the Internet on Aug. 30, 2002 and herein taken as Non-patent Document 19.

The above web documents and Non-patent Document 9 disclose polymethylmethacrylate (PMMA), ABS resins, polycarbonate (PC), polystyrene (PS), Polyethylene (PE), polypropylene (PP), polyacetals (PA) and urethane resins as resin materials. Further, according to the web documents, there seems to be a trial of incorporation into silicone rubber. However, no details are disclosed. About mixture ratios of powder and resins, it is only taught that is the sole disclosure that it is around 10% in weight ratio.

On the other hand, most of complex materials reported in research papers of the discoverer of stress emission, Xu, and others, are mixtures of powder into epoxy resins as matrices, and they are in form of bulk agglomerates. Therefore, strong mechanical force from a vise, for example, is required to induce their emission of light.

In Non-patent Document 10, Xu describes application of his complex materials mainly to technologies for visualizing stress profiles and various types of displays. However, he describes or suggests nothing about development of their applications to artificial light-emitting skins, artificial light-emitting bodies, and the like, for the purpose of entertainment. Additionally, concerning complexing techniques, the sole statement is found in a research paper about epoxy resin molding. Complexing with other resins is not found at all in the web documents either.

As application products of phosphorescent materials developed by Nemoto & Co., Ltd., heretofore known are products from Tokyo Intelligent Network Kabushiki Kaisha (Non-patent Document 20: URL: http://www2.raidway.ne.jp~tin/ accessed through the Internet on Aug. 30, 2002, and Non-patent Document 21: URL: http://www2.raidway.ne.jp/~tin/nl/nl.html accessed through the Internet on Aug. 30, 2002), and products from San Unit Company (Non-patent Document 22: URL: http://web.kyoto-inet.or.jp/people/sansanuc/s4.html accessed through the Internet on Aug. 30, 2002). Non-patent documents 20, 21 demonstrate phosphorescent tiles, phosphorescent straps, phosphorescent special make gel, phosphorescent wallpaper, and so on, as applications of phosphorescent materials. Non-patent document 22 demonstrates applications of phosphorescent materials to tiles, paints, pellets, balls, and so on. However, there is no disclosure or suggestion on developments of applications to artificial light-emitting skins, artificial light-emitting bodies, and the like, for the purpose of entertainment.

Patent Document 20 (Japanese Patent Laid-open Publication JP-1997-95671-A) has no description on stress emission, but proposes transparent phosphorescent materials prepared by using transparent substrates such as glass plates, resin plates, films, and so on, and dispersing therein ultrafine particulate long afterglow inorganic phosphors such as $SrAl_2O_4$:Eu.

Complex materials or sheet-like molded products obtained by the above-introduced and other conventional complexing techniques are too hard for a person to bring about stress emission easily with their own force. Moreover, since the above-mentioned resin-incorporated materials have long afterglow properties, they undesirably appear always luminous, and are difficult to appear luminous only with a touch, for example. Therefore, they have essential difficulties for applications to equipment and materials for entertainment, for example.

OBJECTS AND SUMMARY OF THE INVENTION

It is therefore an object of the invention to overcome these problems.

More specifically, an object of the invention is to provide a complex material easy to emit light even with a human force, such as a finger or hand touch of a person, as well as an artificial light-emitting skin and an artificial light-emitting body using the complex material.

Another object of the invention is to provide a complex material that emits light only when touched, for example, as well as an artificial light-emitting skin and an artificial light-emitting body.

The above and other objects of the invention will be apparent from the description of this specification.

The Inventors conducted vigorous studies toward solution of the problems involved in the prior art techniques. The studies are summarized below.

As discussed above, the following two points are important.

1. The complex material should be soft enough to emit light when touched with a hand or a finger of a person.

2. The complex material should be luminous only when touched.

To fulfill these requirements, it will be effective, for example, 1. to use $SrAl_2O_4$:Eu, or the like, not exhibiting a long afterglow property (of course, $SrAl_2O_4$:Eu emits light under a stress), and 2. for complexing the stress emission material with an elastic material such as a resin, to use an elastic material having a Young's modulus lower than 10 MPa, or further increase the mixture ratio of the stress emission material to the range from 10% to less than 100%, or preferably from 10% to 90%, or more preferably from 30% to 80% by weight.

Through their own researches, by complexing stress emission materials with soft elastic materials such as silicon rubber and organic silicon compounds having siloxane bonds, the Inventors could make a success in bringing about stress emission even with a light hand or finger touch of a person and allowing stress emission only upon such a touch. This was first achieved by the Inventors as far as the Inventors are aware. Based on the technique by the Inventors' own development, they invented an artificial light-emitting skin and an artificial light-emitting body.

According to the first aspect of the invention, there is provided a complex material comprising:

particles which emit light when subjected to a stress; and
an elastic material having a Young's modulus smaller than 10 MPa.

Any kind of stress is acceptable provided the stress emission occurs from particles. Typically, however, the stress is generated by application of an external force. A stress generated by external elastic vibrations or ultrasonic or other waves is herein contemplated as well. In this case, it is presumed that emission of light occurs or the emission intensity changes depending upon the stress change ratio in time. In other words, in case of a stress generated by application of an external force, the complex material emits light depending upon the speed of application or release of the external force. The stress may be pressing stress, shear stress or stretching stress. The shear stress is typically generated between particles and the elastic material. The stress may be generated friction between particles and the elastic material or friction between particles themselves, and causes emission of light.

In the complex material, to ensure stress emission under a weaker force, the elastic material used in combination with the stress emission particles preferably has a Young's modulus equal to or smaller than 1 MPa, or more preferably equal to or smaller than 0.1 MPa. However, if the Young's modulus is excessively small, stress emission will become difficult to occur. Usually, therefore, the Young's modulus is controlled not to underrun 0.0001 MPa. The Young's modulus of the complex material is preferably smaller than 10 MPa, more preferably equal to or smaller than 1 MPa, or more preferably equal to or smaller than 0.1 MPa. Usually, it is controlled to be equal or larger than 0.0001 MPa. The complex material emits light when subjected to compression or pressing stress typically from equal to or larger than 0.1 $kg/cm^2$ to smaller than 100 $kg/cm^2$, typically from equal to or larger than 0.1 $kg/cm^2$ to equal to or smaller than 10 $kg/cm^2$, more typically from equal to or larger than 0.1 $kg/cm^2$ to equal to or smaller than 2 $kg/cm^2$, or still more typically from equal to or larger than 0.5 $kg/cm^2$ to equal to or smaller than 2 $kg/cm^2$.

The elastic material may be selected from those having Young's moduli smaller than 10 MPa, depending upon its intended use. The elastic material may be one kind of such material or a combination of two or more kinds of such materials. The elastic material may be one or more organic materials, one or more inorganic materials, or a combination of both. In this case, the weight percent of the particles in the complex material is controlled preferably from equal to or more than 10% to less than 100%, more preferably from equal to or more than 10% to equal to or less than 90%, or more preferably from equal to or more than 30% to equal to or less than 80%.

Typically, the elastic material is an organic material such as silicone rubber, organic silicon compound having siloxane bonds, synthetic rubber, natural rubber, or the like. Synthetic rubber is polypropylene, polyethylene chloride, or the like. Alternatively, the elastic material may be an organic, electrically conductive substance deformable by acquiring ions. The organic, electrically conductive substances of this type include, for example, electrically conductive polymers having hetero aromatic rings, such as represented by polypyrrole, polythiophene and polyaniline. The elastic material may be a gel such as a polymeric gel, for example. The polymeric gel may be at least one kind of material selected from the group consisting of a water soluble nonelectrolytic polymeric gel having a thermally displaceable function, electrolytic polymeric gel displaceable with pH, combination of a polymeric compound displaceable under an electrical energy with a surfactant, material of the polyvinyl alcohol system, and material of the polypyrrole system, for example. The water-soluble non-electrolytic polymeric gel having a thermally displaceable function is polyvinyl ether or poly N isopropyl acrylamide, for example. The electrolytic polymeric gel displaceable with pH is polyacrylonytrile, for example. The polymeric compound displaceable under an electrical energy is polyacrylamide-2-methyl propane sulfonic acid, for example.

Typical particles that emit light with a stress are inorganic compound particles. The inorganic compound particles contain as its matrix an oxide containing aluminum (Al), gallium (Ga) or zinc (Zn) as a component element, more specifically, an oxide of an alkaline earth metal and aluminum, gallium or zinc as its matrix, and has a non-stoichiometric composition in which the alkaline earth metal element is less than the constant ratio composition with respect to aluminum, gallium or zinc. Alternatively, the particles are prepared by doping a rare earth element such as europium (Eu) or dysprosium (Dy), or a reducing element such as manganese (Mn), vanadium (V) or chromium (Cr) into a matrix of a constant ratio composition or non-stoichiometric composition. One or more kinds of rare earth elements may be doped, depending upon the intended use. When two or more kinds of rare earth elements are doped, typical combination is Eu and Dy, and it is suitable when long after glow is positively used. An example of such inorganic compound particles is $SrAl_2O_4$:Eu particles. A typical example of the complex material is the combination of $SrAl_2O_4$:Eu particles as inorganic compound particles and a silicone resin as the elastic material. The inorganic compound particles may be made of a material doped with manganese (Mn) and/or titanium, such as ZnS:Mn, ZnS:Ti, ZnS:Mn or Ti, other than an oxide containing aluminum, gallium or zinc as one of its components.

In case the inorganic compound particles are made of alkaline earth aluminate, they are an oxide crystal having the general composition formula, $$A_x B_y O_z$$

where
$0.8 \leq x \leq 1.1$
$1.8 \leq y \leq 2.2$
$\{(2x+3y)/2\}-0.2 < z < \{(2x+3y)/2\}+0.2$
$A = Sr_k Ba_l Ca_m Mg_n$
$(0 \leq k, 1, m, n \leq 1, k+1+m+n=1)$
$B = Al_{1-p} D_p \ (0 \leq p < 1)$
$D = Y_q Ga_r In_t \ (0 \leq q, r, t \leq 1, q+r+t=1)$ The term A in the general formula $A_x B_y O_z$ is expressed as $Sr_k Ba_l Ca_m Mg_n$. This means that it is a solid solution containing alkaline earths Sr, Ba, Ca, Mg in any arbitrary composition. D is expressed as $Y_q Ga_r In_t$, and this means that it is a solid solution containing any arbitrary composition of Y, Ga and In. Typically, however, it is a solid solution containing Al as its major component and additionally containing Y, Ga and In. If rare earth elements are doped, they are typically introduced to replace the A site of the oxide crystal to form a solid solution.

The inorganic compound particles may contain, for example, aluminum and silicon (Si) as its components, in lieu of aluminum, gallium or zinc.

The inorganic compound particles may be in $\mu$m size obtained by crushing a solid phase reactant, for example. Preferably, however, crystalline particles having a mean diameter not larger than 100 nm, or especially from equal to or larger than 5 nm to equal to or smaller than 100 nm are used. When the complex material is made of crystalline inorganic compound particles and an elastic material, the elastic material is typically amorphous.

The complex material may be entirely a gel, depending upon the intended use.

From the standpoint of coupling the stress emission particles and the elastic material more firmly to facilitate generation of a stress enough to cause stress emission of the particles upon application of an external force, or the like, a binder is preferably used to couple the particles with the elastic material. This is especially effective when the particles are inorganic compound particles and the elastic material is an organic material. Essentially, the binder may be any kind of binder provided it enhances the adhesion than direct contact between the particles and the elastic material. In a concrete example, particles surface-treated by a silane coupling agent are used as the particles. Alternatively, a silane coupling agent is added to an organic material used as the elastic material, and it is complexed with the particles. From the standpoint of enhancing the adhesion between the particles and the elastic material, surfaces of the particles are coated by silica.

The features of the first aspect of the invention summarized above are applicable to the second to twelfth aspects of the invention as well, as far as they are congruous to their natures.

According to the second aspect of the invention, there is provided a complex material comprising:
particles which emit light when subjected to a stress; and an elastic material,
wherein a binder of the particles and the elastic material exists between them.

According to the third aspect of the invention, there is provided a complex material comprising:
particles which emit light when subjected to a stress; and an elastic material,
wherein emission of light occurs when a shear stress is generated in the particles.

According to the fourth aspect of the invention, there is provided a complex material comprising:
particles which emit light when subjected to a stress; and an elastic material,
wherein emission of light occurs when a shear stress is generated between the particles and the elastic material.

According to the fifth aspect of the invention, there is provided a complex material comprising:
particles which emit light when subjected to a stress; and an elastic material,
wherein emission of light occurs when friction occurs between the particles and the elastic material.

According to the sixth aspect of the invention, there is provided a complex material comprising:
particles which emit light when subjected to a stress; and an elastic material,
wherein emission of light occurs when friction occurs between the particles.

According to the seventh aspect of the invention, there is provided a complex material comprising:
particles which emit light when subjected to a stress; and an elastic material,
wherein emission of light occurs when a compressing stress is generated between the particles and the elastic material.

According to the eighth aspect of the invention, there is provided a complex material comprising:
particles which emit light when subjected to a stress; and an elastic material,
wherein emission of light occurs when a tensile stress is generated between the particles and the elastic material.

According to the ninth aspect of the invention, there is provided an artificial light-emitting skin made of a complex material comprising:
particles which emit light when subjected to a stress; and an elastic material having a Young's modulus smaller than 10 MPa.

According to the tenth aspect of the invention, there is provided an artificial light-emitting skin made of a complex material comprising:
particles which emit light when subjected to a stress; and an elastic material,
wherein a binder of the particles and the elastic material exists between them.

According to the eleventh aspect of the invention, there is provided an artificial light-emitting body made of a complex material comprising:
particles which emit light when subjected to a stress; and an elastic material having a Young's modulus smaller than 10 MPa.

According to the twelfth aspect of the invention, there is provided an artificial light-emitting body made of a complex material comprising:
particles which emit light when subjected to a stress; and an elastic material,
wherein a binder of the particles and the elastic material exists between them.

In the present invention, appropriate ones of the above-summarized aspects of the invention may be combined is so desired. Furthermore, artificial light-emitting hair, for example, can be made by using those complex materials.

The artificial hair is not limited in thickness provided it readily emits light when touched by a hand of a finger of a person. However, from the standpoint of keeping it soft, causing an internal stress necessary for stress emission and having it emit light easily, and simultaneously giving favorable tactile impression to a person, the thickness is preferably not more than 2 mm, more preferably not thicker than 1 mm, and still more preferably not thicker than 0.5 mm. Normally, it does not underrun 0.1 mm.

Complex materials, artificial light-emitting skins and artificial light-emitting bodies according to the invention are suitable for applications to bodies of various kinds of robots (working robots, amusement robots, consolation robots, etc.), various kinds of home electronic products such as audio apparatuses (including speakers), TV sets, video apparatuses, personal computers, and so on.

According to the invention summarized above, by controlling the Young's modulus of the elastic material to smaller than 10 MPa, preferably to not larger than 1 MPa, or more preferably to not larger than 0.1 MPa in the complex material of the stress emission particles and the elastic material, it is ensured that emission of light is brought about with a light touch of a person's hand or finger. Further, emission stops immediately when the touch is removed.

Moreover, because of the existence of the binder between the stress emission particles and the elastic material, their adhesion can be enhanced even when the particles are inorganic compound particles while the elastic material is an organic material, and a stress necessary for emission can be generated easily by application of an external force or the like.

BRIEF DESCRIPTION OF THE DRAWINGS

FIG. 6 is a schematic diagram showing a layout used in an emission test of the complex sheet according to the first embodiment of the invention;

FIGS. 7A and 7B are schematic diagrams for explaining the emission mechanism of the complex sheet according to the first embodiment of the invention;

DETAILED DESCRIPTION OF THE PREFERRED EMBODIMENTS

Before explanation of embodiments of the invention, features of the invention are briefly explained below.

Figure 1:
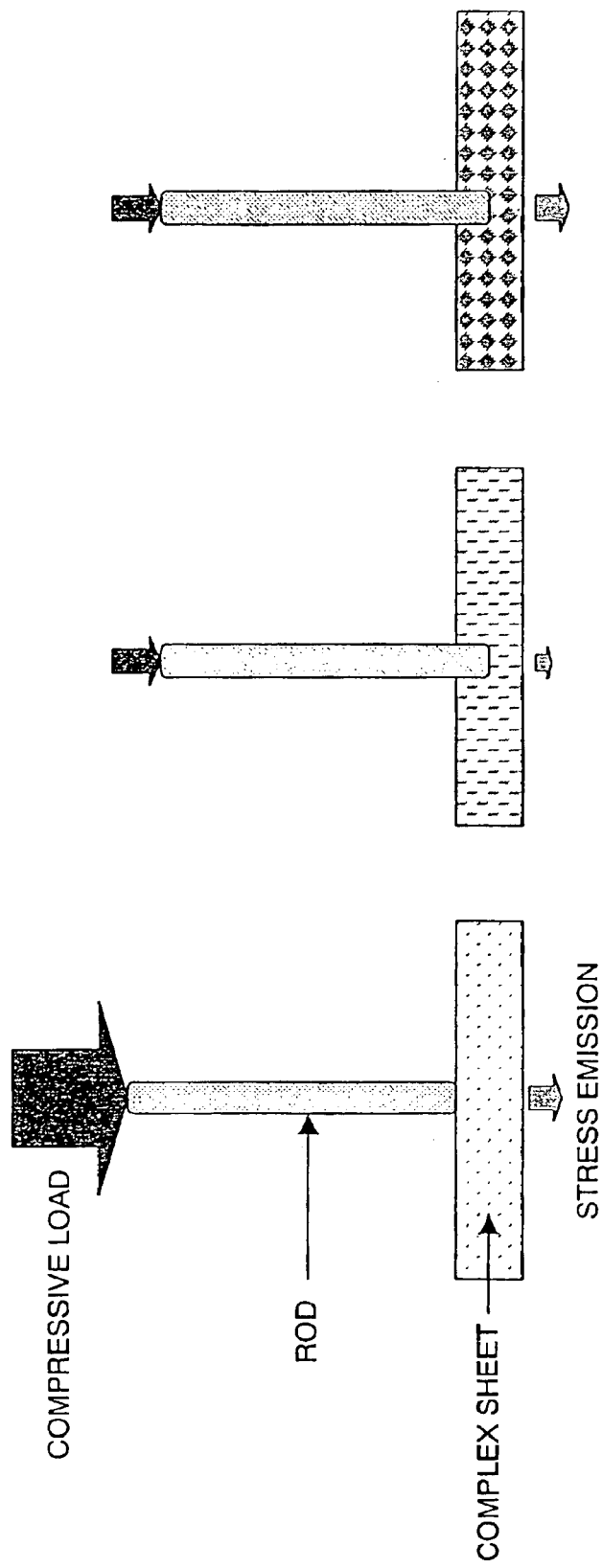
FIGS. 1A through 1C are schematic diagrams for explaining features of the present invention.

FIG. 1A shows that a pressure is applied through a rod to a complex sheet comprising an epoxy-resin complex material prepared by complexing a relatively hard epoxy resin and stress emission particles of $SrAl_2O_4$:Eu or the like. The epoxy resin has a Young's modulus around tens MPa, and the epoxy-resin complex material has a Young's modulus around 100 MPa. In order to bring about stress emission with this complex sheet, it is necessary to apply as high pressure as approximately 100 kg/cm² to the complex sheet. Therefore, it is impossible for a person to bring about stress emission only with his/her hand or finger touch.

FIG. 1B shows that a pressure is applied via a rod to a complex sheet comprising a complex material prepared by complexing a soft elastic material having a Young's modulus smaller than 10 MPa (for example, silicone resin) and stress emission particles of $SrAl_2O_4$:Eu or the like. In order to bring about stress emission with this complex sheet, it is sufficient to apply a pressure around 1 kg/cm², for example, to the complex sheet. Therefore, stress emission can be brought about sufficiently with a person's hand or finger touch.

FIG. 1C shows that a pressure is applied via a rod to a complex sheet comprising a complex material prepared by complexing a soft elastic material having a Young's modulus smaller than 10 MPa (for example, silicone resin) and stress emission particles of $SrAl_2O_4$:Eu or the like after treating surfaces of the stress emission particles to enhance heir adhesion to the elastic material. Here again, similarly to the case of FIG. 1B, it is sufficient to apply a pressure around 1 kg/cm² to the complex sheet. However, the emission intensity is larger than that of FIG. 1B. This is because the surface treatment enhances adhesion between the elastic material and the stress emission particles and allows easier transmission of the applied pressure to the stress emission particles.

Hereunder, embodiments of the invention will be explained with reference to the drawings.

Figure 2:
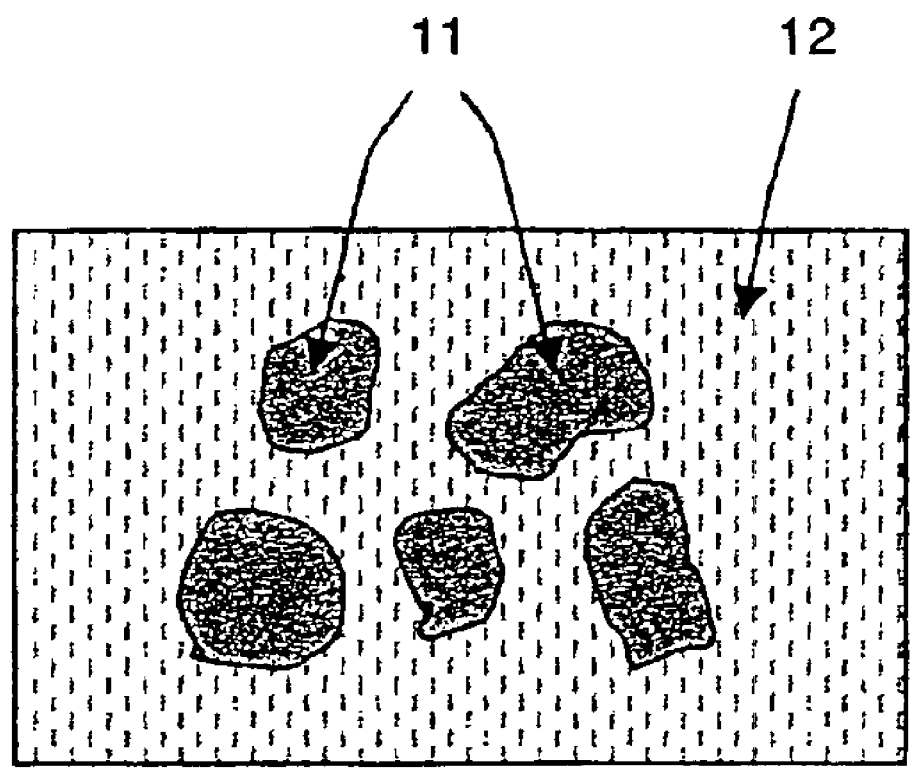
FIG. 2 is a cross-sectional view of a complex sheet according to the first embodiment of the invention.

FIG. 2 shows a complex sheet according to the first embodiment of the invention. As shown in FIG. 2, the complex sheet is a sheet of a complex material of stress emission particles 11 of $SrAl_2O_4$:Eu and an elastic material 12. The elastic material 12 is a soft organic material having a Young's modulus smaller than 10 MPa, preferably equal to or smaller than 1 MPa, or more preferably equal to or smaller than 0.1 MPa, and normally not smaller than 0.0001 MPa. Practically, it may be silicone rubber, organic silicon compound having siloxane bonds, synthetic rubber, natural rubber, or the like. Weight percent of the stress emission particles 11 in the complex material is from equal to or more than 10% to less than 100%, preferably from equal t or more than 10% to less than 90%, or more preferably from equal to or more than 30% to equal to r less than 80%. Diameter of each stress emission particle 11 may be, for example, μm size or smaller. For example, it may be from equal to or smaller than 100 nm to equal to or larger than 5 nm. Although the Young's modulus of the complex material depends upon the weight percent of the stress emission particles 11, it will roughly be several times the Young's modulus of the elastic material. However, similarly to the elastic material 12, it is preferably smaller than 10 MPa, more preferably equal to or smaller than 1 MPa, or still preferably equal to or smaller than 0.1 MPa, and normally equal to or larger than 0.0001 MPa.

Next explained is a manufacturing method of this complex sheet.

First prepared is $SrAl_2O_4$:Eu ceramics by normally used solid-phase reaction.

Procedures for preparation were started with mixing measured amounts of the following substances as source materials in a ball mill for approximately 20 hours.

$SrCO_3$ 0.39 mol=147.6292×0.39
=57.5753888 g
$Al_2O_3$ 0.40 mol=101.96128×0.4
=40.784512 g
$Eu_2O_3$ 0.002 mol=351.9182×0.002
=0.7038396 g
$B_2O_3$ 0.032 mol=69.6182×0.032
=2.2277824 g Thereafter, the source materials were synthesized through the processes of calcination in oxygen at 1400° C. and reducing thermal treatment in $H_2$(4%)-$N_2$ atmosphere at 1300° C., and the intended monoclinic composite $SrAl_2O_4$:Eu was obtained.

An X-ray diffraction figure of the composite obtained was measured and compared with the result of a known article, "F Hanic, T. Y. Chemekova and J. Majling, J. Appl. Phys., 12 (1979) 243". Then, all peaks coincided, and it was confirmed to have a single phase.

Figure 3A:
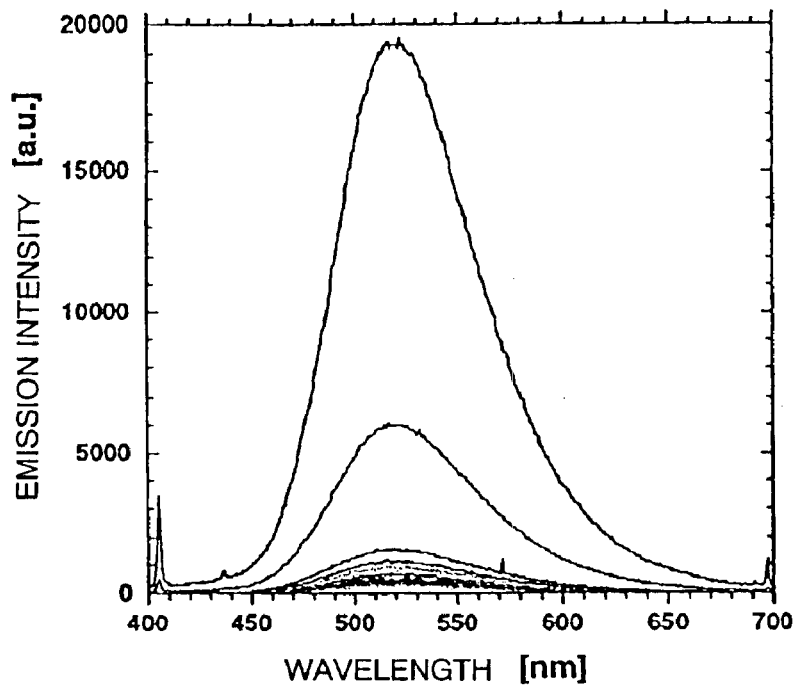
FIGS. 3A and 3B are schematic diagrams showing ultraviolet-excited emission spectrum of $SrAl_2O_4$:Eu powder and its afterglow characteristics.
Figure 3B:
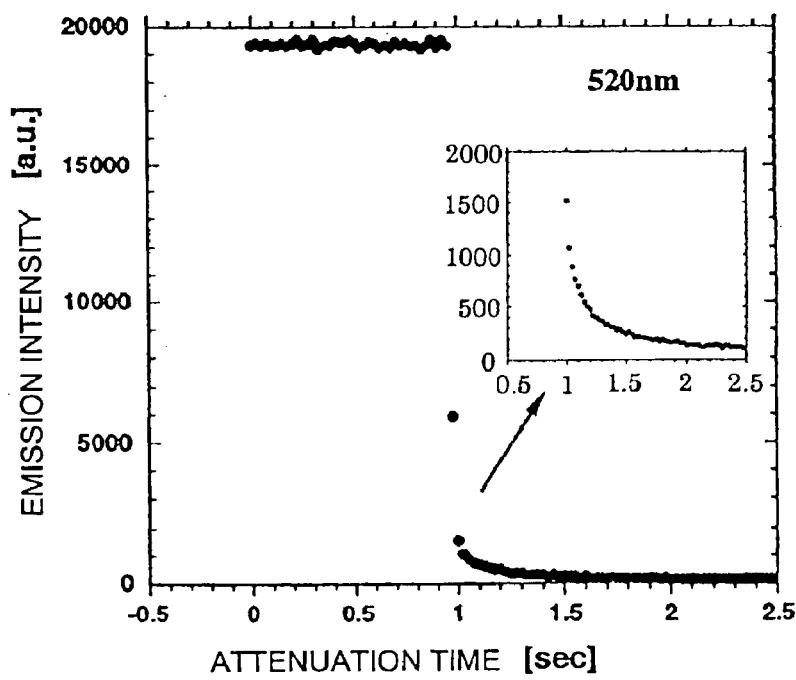
Figure 4A:
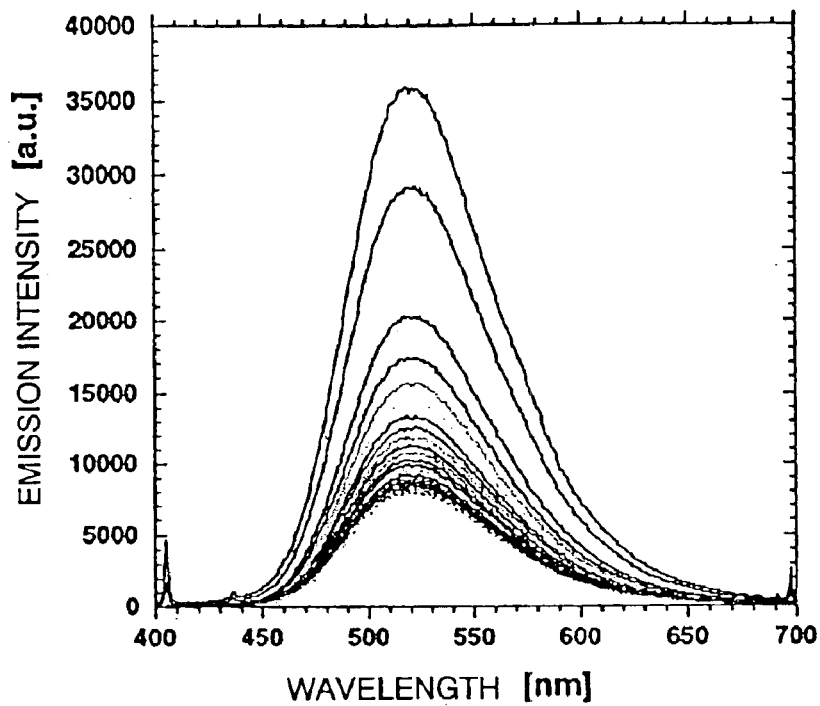
FIGS. 4A and 4B are schematic diagrams showing ultraviolet-excited emission spectrum of $SrAl_2O_4$:Eu+Dy powder and its afterglow characteristics.
Figure 4B:
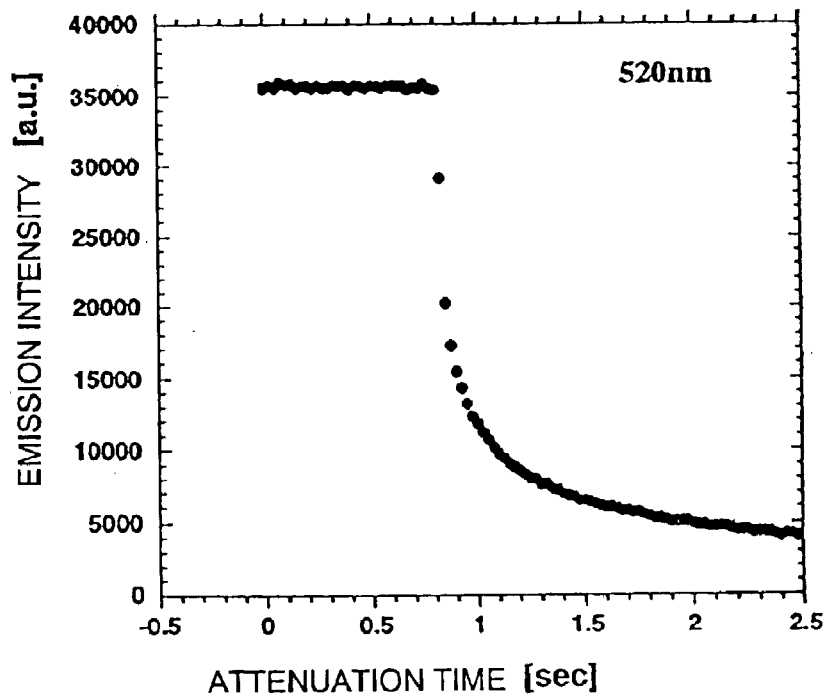

FIG. 3A shows ultraviolet-excited emission spectrum of $SrAl_2O_4$:Eu prepared by the Inventors, and FIG. 3 shows its afterglow characteristics. FIG. 4A shows ultraviolet-excited emission spectrum of $SrAl_2O_4$:Eu+Dy powder (from Nemoto & Co., Ltd. under the brand name of LumiNova (G-300C)), and FIG. 4B shows its afterglow characteristics.

From FIGS. 3A, 3B, 4A and 4B, it can be confirmed that main peaks of emission appear in wavelengths near 520 nm, and the light is green in any of the samples. However, as to afterglow (or decay) characteristics after removal of irradiation of ultraviolet rays, it can be confirmed that the emission intensity of $SrAl_2O_4$:Eu is attenuated much faster. In FIGS. 3A and 4A showing emission spectra, values measured every 25 milliseconds are plotted. It is appreciated here that intensities of emission spectra degrade every moment.

Figure 5:
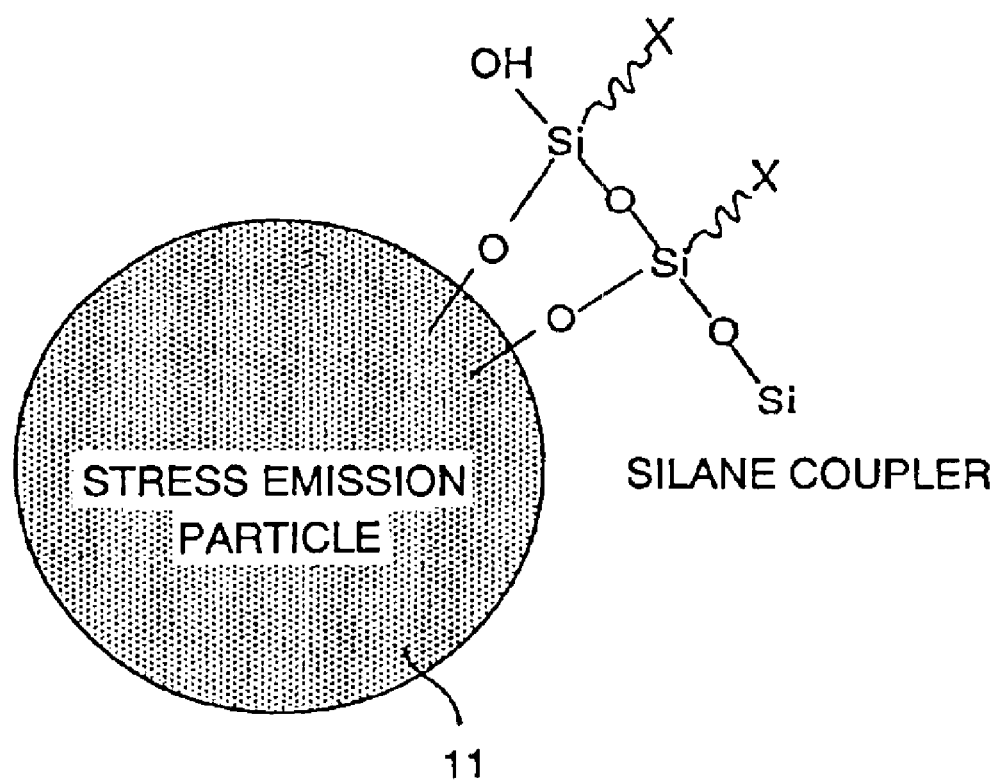
FIG. 5 is a schematic diagram showing the surface of a stress emission particle treated with a silane coupling agent according to the first embodiment of the invention.

After that, by crushing the $SrAl_2O_4$:Eu crystal obtained, powder of $SrAl_2O_4$:Eu controlled in grain size to have a predetermined mean grain size is obtained. Then, the $SrAl_2O_4$: Eu powder and a silane coupling agent are stirred in a predetermined solvent such as ethanol to process surfaces of $SrAl_2O_4$:Eu particles as the stress emission particles 11 with the silane coupling agent (FIG. 5). The silane coupling agent is a compound expressed by X-Si $(OR)_3$ (where X is an amino group, vinyl group or epoxy group, and OR is a hydrolyzable group such as a methoxy group or ethoxy group, and there are two different reactive groups in the molecule. There are a number of kinds of silane coupling agent different in X. Since OR is a hydrolyzable group such as a methoxy or ethoxy group, for example, the silane coupling agent functions as a binder between organic materials (here is the elastic material 12) and inorganic materials (here is the stress emission particles 11) that are normally difficult to couple. Mechanisms of adhesion between an organic material like an organic resin and an inorganic material by the silane coupling agent are chemical bonding with the organic material, hydrogen bonding with the organic material, improvement of the affinity to the organic material, improvement of the compatibility to the organic material, and so forth.

Thereafter, the powder of the stress emission particles 11 after surface treatment with the silane coupling agent and the organic material used as the elastic material 12 are mixed in a mixer, and the slurry after degassed in a vacuum is poured into a die, and cured into a soft complex sheet.

Next explained is the result of an emission test carried out with the complex sheet according to the first embodiment. For preparing the complex sheet used in the test, γ-glycidoxypropyl trimethoxy silane was used as the silane coupling agent, and a silicone resin (KE106 from Shin-etsu Silicon) was used as the elastic material 12. The mixture ratio of $SrAl_2O_4$:Eu powder and the silicon resin was 1:1 in weight. The mean grain size of the $SrAl_2O_4$:Eu powder is 2 μm. Young's modulus of this complex sheet was approximately 0.012 MPa. This is about 1/10000 of a complex sheet using an epoxy resin as the elastic material 12. The silicon resin (KE106 from Shin-etsu Silicon) contains poly-dimethyl siloxane as its major component, and various kinds of silicon resins different in Young's modulus and hardness can be obtained by controlling the molecular mass of poly-dimethyl siloxane. Gel substances can be obtained from this silicon resin as well.

FIG. 6 shows a layout used in an emisson test of the complex sheet according to the first embodiment of the invention. As shown in FIG. 6, the complex sheet is put on one of surfaces of a transparent glass plate. While the complex sheet is photographed with a video camera through the transparent glass plate from the other surface thereof in a dark place, a pressure is applied to the complex sheet. The pressure applied is measured with a force sensor. The complex sheet was compressed in three kinds of ways. In the first way, a metal ring was put on the complex sheet, and a pressure was applied to the complex sheet by urging the metal ring with one end of the force sensor rod. In the second way, the complex sheet was compressed directly with a person's finger. In the third way, a metal rod was laid on the complex sheet, and a pressure was applied to the complex sheet by urging the metal rod with one end of the force sensor rod. In each of the compression through the metal ring, the compression with the finger, and the compression with the metal rod emission of light was observed at the moment of application and removal of the pressure to and from the complex sheet even with a light load of 100 to 300 g. As already explained, the complex sheet using the epoxy resin does not emit light when subjected to this light level of load.

Next explained is the mechanism of bringing about emission of sufficiently intensive light by application of a pressure with the light load to the complex sheet as mentioned berore. FIG. 7A shows the complex sheet before subjected to a pressure. FIG. 7B shows the complex sheet when subjected to a pressure. As shown in FIG. 7B, when the complex sheet is compressed by a pressure, a shear force works on the interface between the stress emission particles 11 and the elastic material 12, and a shear stress generated thereby causes emission of light. Additionally, emission by friction between the stress emission particles 11 and the elastic material 12 and emission by frictional contacts among stress emission particles 11 having moved closely to each other also contribute to the stress emission observed.

As explained above, according to the first embodiment, the stress emission particles 11 of $SrAl_2O_4$:Eu is surface-treated by the silane coupling agent, and thereafter, the complex sheet is prepared by complexing the particles 11 with the elastic material 12 of a soft organic material, such as silicone rubber, having a Young's modulus smaller than 10 MPa, preferably not larger than 1 MPa or more preferably not larger than 0.1 MPa. Thereby, it is possible to realize the complex sheet capable of emitting light of sufficient intensity even with a light hand or finger touch of a person and capable of emitting light only when touched.

Next explained is the second embodiment of the invention.

Figure 8:
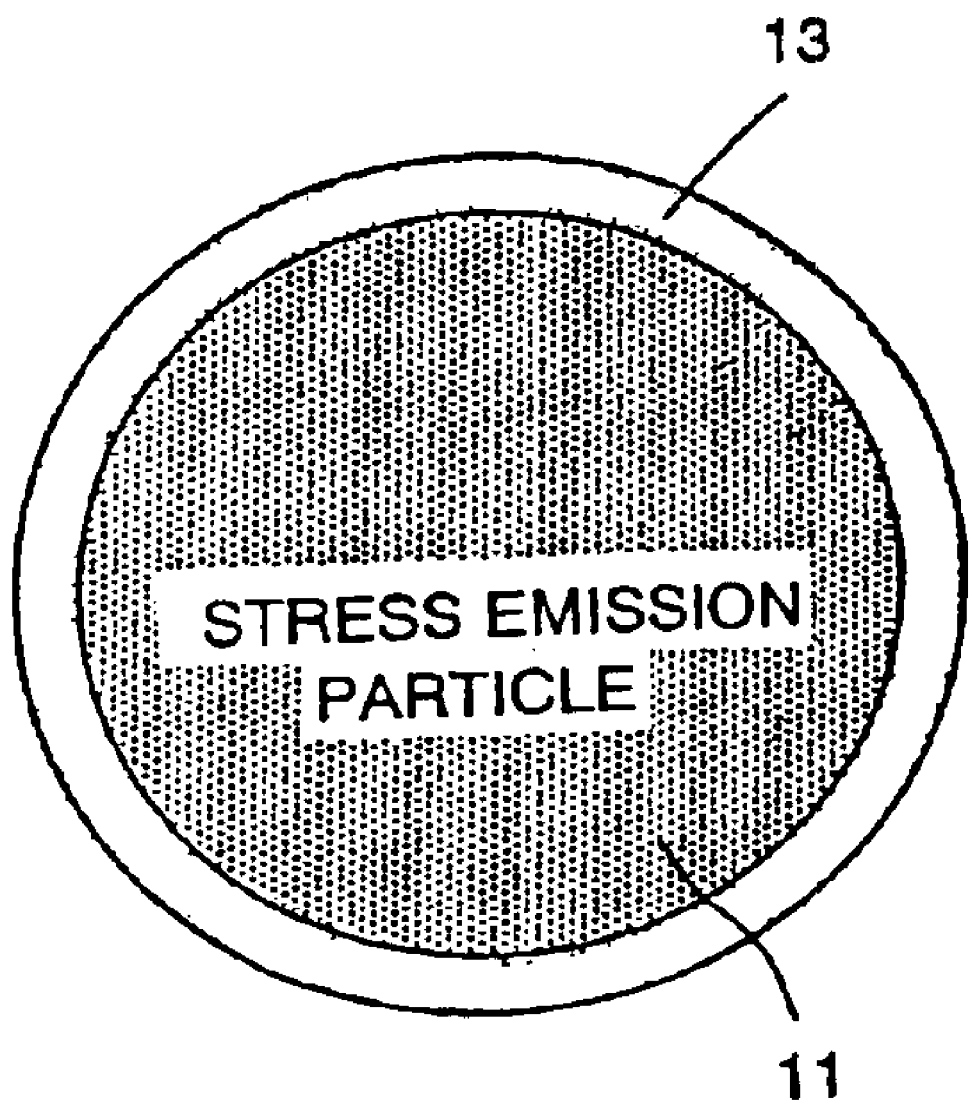
FIG. 8 is a schematic diagram showing the surface of a stress emission particle coated by silica according to the second embodiment of the invention.

In the second embodiment, surfaces of the stress emission particles 11 are coated by silica 13 as shown in FIG. 8. Then, after the surface of the silica 13 is treated with a silane coupling agent, the stress emission particles are complexed with the elastic material 12. The other features of the first embodiment are common to those of the first embodiment. Therefore, their explanation is omitted here.

According to the second embodiment, the silica 13 coating the surfaces of the stress emission particles 11 binds more firmly with the silane coupling agent than the stress emission particles 11 themselves. Therefore, the second embodiment enhances adhesion between the stress emission particles 11 and the elastic material 12, and therefore allows easier emission of light with a light hand or finger touch of a person to the complex sheet.

Next explained is the third embodiment of the invention.

The first and second embodiments rely on application of a pressure to the complex sheet to bring about emission of light. The third embodiment, however, is directed to stretching the complex sheet in parallel to its surface for bringing about emission of light.

More specifically, the third embodiment brings about stress emission by stretching the complex sheet identical to the first embodiment in parallel to its surface. The emission mechanism will be as explained below. When the complex sheet is stretched in parallel to its surface, it is compressed in thickness. Due to expansion in area of the complex sheet and its compression in thickness, a shear stress is generated on the interface between the stress emission particles 11 and the elastic material 12, or friction occurs between the stress emission particles 11 and the elastic material 12 or between the stress emission particles 11 themselves. As a result, light is emitted.

Next explained is a result of an emission test by application of a tensile or stretching force to the complex sheet. For preparation of the complex sheet used in the test, γ-aminopropyl methoxy silane was used as the silane coupling agent, and a silicone resin (KE106 from Shin-etsu Silicon) was used as the elastic material 12. The mixture ratio of $SrAl_2O_4$:Eu powder and the silicon resin was 1:1 in weight. The mean grain size of the $SrAl_2O_4$:Eu powder is 2 μm. Young's modulus of this complex sheet was approximately 0.012 MPa. This is about 1/10000 of a complex sheet using an epoxy resin as the elastic material 12. The complex sheet is 5 mm wide, 10 mm long and 0.3 mm thick.

Figure 9C:
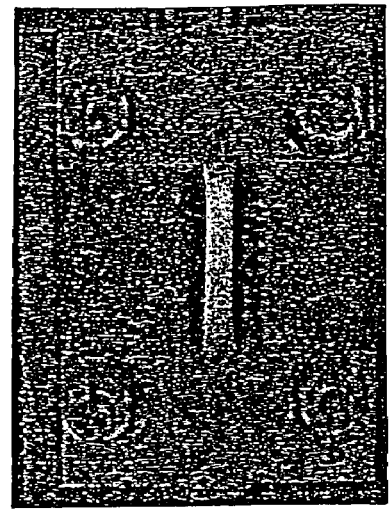
FIGS. 9A through 9C are photographs in substitution for drawings, which show a result of an emission test of a complex sheet by stretch according to the third embodiment of the invention.
Figure 9B:
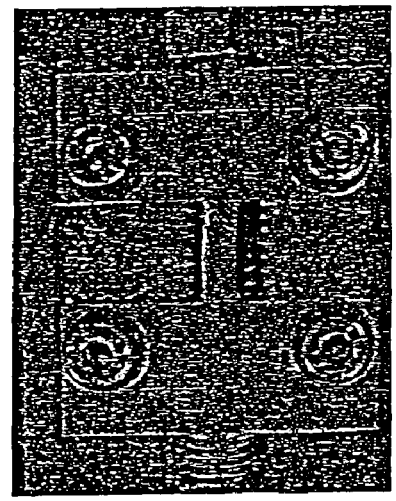
Figure 9A:
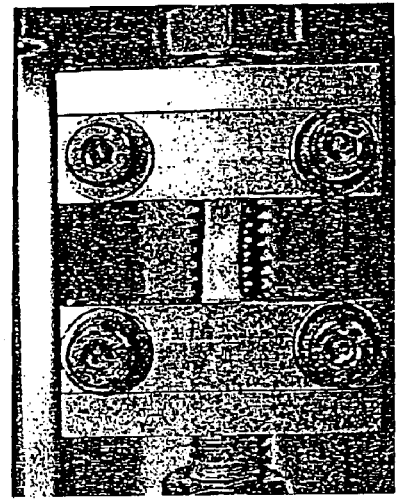

FIGS. 9A through 9C show how the test was conducted and resulted. As shown in FIG. 9A, opposite lengthwise ends of the complex sheet are fixed to a pair of stretchers. FIG. 9A is a photograph taken in a bright place, but FIG. 9B is a photograph taken in a dark room. FIG. 9C is a photograph taken when the stretchers are moved away in opposite directions at the speed of 50 mm/sec and stretch the complex sheet in parallel to its plane to a double the original length. The photograph clearly shows that emission occurred at the instance where the complex sheet is stretched. The stretching load applied to the complex sheet was approximately 1.2 N.

Figure 10:
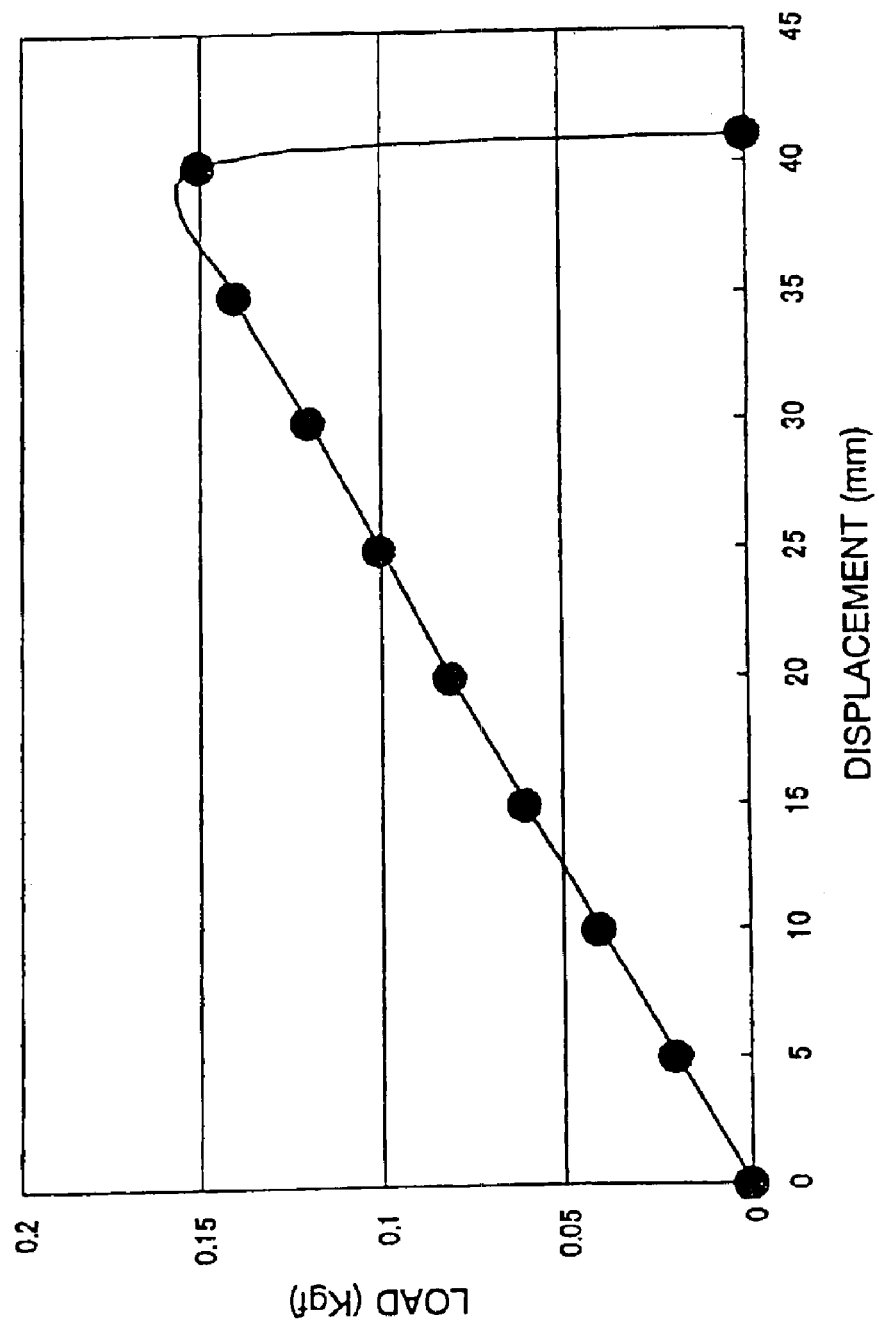
FIG. 10 is a schematic diagram showing a result of measurement of load-to-distortion characteristics of the complex sheet according to the third embodiment of the invention.

Load-to-distortion characteristics of this complex sheet were measured. FIG. 10 shows its result. It can be said from FIG. 10 that the complex sheet using silicone rubber as the elastic material 12 is a rubber like material expandable from the original length of 10 mm to approximately 40 mm, that is, by as long as approximately four times.

As explained above, according to the third embodiment, stress emission can be brought about by lightly stretching the complex sheet in parallel to its plane.

Next explained is the fourth embodiment of the invention. The fourth embodiment is directed to application of the above-explained complex sheet to an artificial light-emitting skin.

Figure 11:
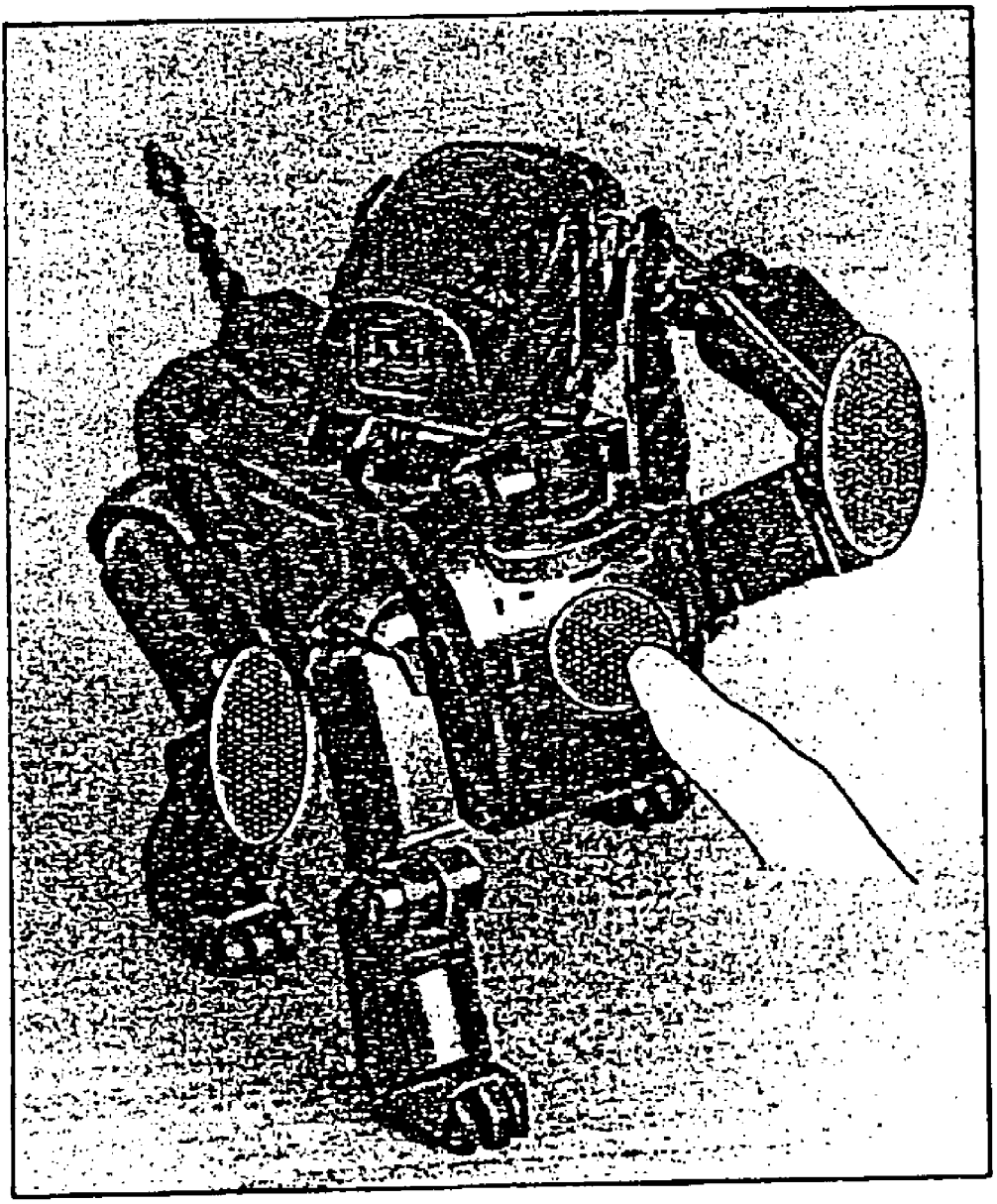
FIG. 11 is a schematic diagram showing the aspect of an entertainment dog-shaped robot on which complex sheets are affixed as an artificial light-emitting skin.

As shown in FIG. 11, in the fourth embodiment of the invention, the complex sheets are affixed as an artificial light-emitting skin onto the breast and joints of legs of a dog-shaped entertainment robot. The complex sheet on the breast emits light with a light finger touch of a person. On the other hand, the complex sheets on the leg joints emit light when they expand and contract in parallel to their planes upon bending and stretching movements of the legs.

As explained above, according to the fourth embodiment, emission of light can be brought about from knees in response to movements of the dog-shaped robot, and additionally, emission can be brought about from the breast by a user's touch on it. Therefore, the user can enjoy emission of light in addition to movements of the dog-shaped robot. As such, it is possible to provide the very charming dog-shaped robot that induces a user's feeling of comfortableness or loveliness, and stimulates the user's sensitivity.

The invention has been explained heretofore by way of some embodiments. However, the embodiments should not be construed to limit the invention, but the invention contemplates various changes or modifications within its technical concept as well.

For example, numerical values, structures, shapes, materials, source materials, processes, and others are not but examples. Other acceptable numerical values, structures, shapes, materials, source materials and processes may be employed alternatively.

As described above, according to the present invention, the complex material is made of particles capable of emitting light under a stress in combination with an elastic material whose Young's modulus is not larger than 10 MPa. Therefore, the invention realizes a complex material, artificial light-emitting skin and artificial light-emitting body with which a person can bring about emission of light with his/her light hand or finger touch or stretching force and only by applying such a touch or stretching force.

Then, the complex material leads to large innovation in the field of entertainment or amusement robots and other various fields.

What is claimed is:

1. An artificial light emitting skin, comprising:

an elastic material matrix and crystalline $SrAl_2O_4$:Eu particles that emit light when a mechanical stress generated by an external force is applied thereto and having a mean diameter of 5 nm, the crystalline $SrAl_2O_4$:Eu particles prepared by
mixing 0.39 $SrCO_3$ mol, 0.40 $Al_2O_3$ mol, 0.002 $Eu_2O_3$ mol, and 0.032 $B_2O_3$ mol as source materials in a ball mill for 20 hours,
synthesizing the source materials via calcination in oxygen at 1400° C., and
reducing thermal treatment in $H_2$(4%)-$N_2$ atmosphere at 1300° C.;

a coating agent that coats the surfaces of the crystalline $SrAl_2O_4$:Eu particles, said coating agent including at least one of silane or silica; and wherein the silica and silane coated $SrAl_2O_4$:Eu particles comprise 30% to 80% of the artificial light emitting skin by weight percent, the artificial light emitting skin has a thickness of 0.1 mm and a Young's modulus of 0.0001 MPa, and the artificial light emitting skin emits light detectable by a naked eye when subjected to a compression stress of 0.1 kg/cm².

* * * * *

UNITED STATES PATENT AND TRADEMARK OFFICE
CERTIFICATE OF CORRECTION

PATENT NO. : 6,932,920 B2
DATED : August 23, 2005
INVENTOR(S) : Junichi Toyoda et al.

It is certified that error appears in the above-identified patent and that said Letters Patent is hereby corrected as shown below:

Title page,
Item [73], Assignee, change "Son Corporation" to -- Sony Corporation --.

Column 2,
Line 16, change "http//www.aist.go.jp/aist$_{13}$" to -- http//www.aist.go.jp/aist_ --.

Column 12,
Line 42, change "berore" to -- before --.

Signed and Sealed this

Twentieth Day of December, 2005

JON W. DUDAS
*Director of the United States Patent and Trademark Office*